United States Patent
Yuan et al.

(10) Patent No.: US 11,298,390 B2
(45) Date of Patent: Apr. 12, 2022

(54) **TOTAL FLAVONOIDS EXTRACT OF *GYNURA FORMOSANA* KITAM., PREPARATION METHOD THEREFOR AND USE THEREOF FOR TREATING HYPERURICEMIA**

(71) Applicant: ZHANGZHOU PIEN TZE HUANG PHARMACEUTICAL CO., LTD., Fujian (CN)

(72) Inventors: Huijun Yuan, Fujian (CN); Tingting Yin, Fujian (CN); Fei Hong, Fujian (CN); Juan Yu, Fujian (CN); Jinxiang Zeng, Fujian (CN); Shicong Wang, Fujian (CN)

(73) Assignee: Zhangzhou Pien Tze Huang Pharmaceutical Co., Ltd., Fujian (CN)

( * ) Notice: Subject to any disclaimer, the term of this patent is extended or adjusted under 35 U.S.C. 154(b) by 79 days.

(21) Appl. No.: 16/821,314

(22) Filed: Mar. 17, 2020

(65) Prior Publication Data
US 2020/0222484 A1 Jul. 16, 2020

Related U.S. Application Data

(63) Continuation of application No. PCT/CN2018/101168, filed on Aug. 17, 2018.

(30) Foreign Application Priority Data

Sep. 18, 2017 (CN) .......................... 201710841633.9

(51) Int. Cl.
*A61K 36/00* (2006.01)
*A61K 36/28* (2006.01)
*A61P 19/06* (2006.01)

(52) U.S. Cl.
CPC .............. *A61K 36/28* (2013.01); *A61P 19/06* (2018.01)

(58) Field of Classification Search
CPC ...................................................... A61P 19/06
See application file for complete search history.

(56) References Cited

U.S. PATENT DOCUMENTS

| 2020/0215140 A1 | 7/2020 | Chen et al. |
| 2020/0215141 A1 | 7/2020 | Chen et al. |

FOREIGN PATENT DOCUMENTS

| CN | 1565464 | A | 1/2005 |
| CN | 101336949 | A | 1/2009 |
| CN | 104013659 | A | 9/2014 |
| CN | 104151380 | A | 11/2014 |
| CN | 104173458 | A | 12/2014 |
| CN | 107582587 | A | 1/2018 |
| CN | 107582588 | A | 1/2018 |
| CN | 107582589 | A | 1/2018 |
| CN | 107582590 | A | 1/2018 |
| CN | 107625800 | A | 1/2018 |
| JP | 2003171283 | A | 6/2003 |
| JP | 2008092869 | A | 4/2008 |

OTHER PUBLICATIONS

Shaw et al., Gynura formosana extract decreases serum uric acid and urine albumin in mice fed with high-fat diet. Annals of Nutrition and Metabolism, (2013) vol. 63, Supp. SUPPL. 1, pp. 1668. Abstract No. PO2911 (Year: 2013).*
Chen, Beneficial effect of rutin on oxonate-induced hyperuricemia and renal dysfunction in mice. Pharmacology, (2013) vol. 92, No. 1-2, pp. 75-83 (Year: 2013).*
International Search Report, International Application No. PCT/CN2018/101167.
Written Opinion dated Nov. 2018, Application No. PCT/CN2018/101167.
English Translation of the First Office Action, dated Mar. 30, 2020, Application No. 201710840946.2.
Luo, Y., "Introduction to Food Biotechnology," China Agricultural University Press, pp. 325-326 (Aug. 31, 2016).
Zhang, R., "Practical Ophthalmic Pharmacology," People's Military Medical Press, p. 388, Sep. 30, 2015.
Zhang, X., Selected Questions and Answers of Shanghai Sannong Service Hotline, p. 72.
Pan, R., et al., "Rutin Inhibits Oleic Acid Induced Lipogenesis in Hepatocyte Cells Via Regulating TG Metabolic Pathway," Journal of Yunnan University of Traditional Chinese Medicine, vol. 38, No. 5, (2015).
Yao, L., et al., "Research Process of Chemical Constituents and Biological Activities of the Genus *Gynura* Plants," Journal of Northern Horticulture, No. 24, (2016) (English translation).
Wan, Y., "Therapeutical Effect of Gynura Formosana Alcohol Extract on Nonalcoholic Fatty Liver Disease in Rats," GJICMWM, vol. 2, No. 2 (2014).

(Continued)

*Primary Examiner* — Qiuwen Mi
(74) *Attorney, Agent, or Firm* — Elmore Patent Law Group, P.C.; Joseph Zucchero; Carolyn Elmore

(57) ABSTRACT

Disclosed is a total flavonoids extract of *Gynura formosana* Kitam., containing 80%-85% of rutin by weight percent content. The results of pharmacological experiments show that the extract can lower the activity of xanthine oxidase in the liver of a hyperuricemia model mouse and reduce the synthesis of uric acid to a certain degree and has a certain uric acid-lowering effect, and can be used as a potential drug for treating hyperuricemia or gout. The method for preparing the total flavonoids extract of *Gynura formosana* Kitam. comprises: after an extraction step, selecting a complex enzyme composed of enzymes with a specific composition and a specific ratio for enzymolosis, and further carrying out the step of extracting and concentrating with macroporous resin and isolating and purifying with macroporous resin, so that the HPLC purity of rutin in the resulting total flavonoids extract of *Gynura formosana* Kitam. reaches 80%-85%.

16 Claims, 2 Drawing Sheets

(56) References Cited

OTHER PUBLICATIONS

Wong, L., "Effect of Total Flavonoids in *Gynura divaricata* (L.) DC. on Blood Lipid and Liver of Rats with Hyperlipidemia," Capital Journal of Public Health, vol. 10, No. 5 (2016).

English Translation of Second Office Action issued in priority Chinese Application No. 2017108416339.

Lin, Y., et al., "Optimization the Extraction of Total Flavonoids from Gynua formosana Kitam Guided by Ultrasound and Research on its Antibacterial Activity in vitro," Journal of Youjiang Medical University for Nationalities, vol. 39, No. 2, pp. 90-93, Apr. 2017.

English translation of First Office Action, dated Aug. 3, 2021 in JP2020-537273.

English translation of First Office Action, dated Oct. 26, 2021 in KR10-2020-7011228.

English Translation of the Third Office Action, dated Dec. 28, 2020, in CN201710841633.9.

Hou, W. C. et al., "The Phenolic Constituents and Free Radical Scavenging Activities of Gynura formosana Kiamnra", J. Sci. Food Agric., 85, DOI: 10.1002/jsfa.2017, 2005, 615-621.

Nagao, A. et al., "Inhibition of Xanthine Oxidase by Flavonoids", Biosci. Biotechnol. Biochem., 63(10), 1999, 1787-1790.

Vanijajiva, O. et al., "A revision of Gynura (Asteraceae: Senecioneae)", JSE, 49(4), https://doi.org/10.1111/j.1759-6831.2011.00139.x, Jun. 2011, 285-314.

Wang, C. et al., "Treatment of Chronic Illness", in Clinical Practice of Functional Medicine, Xi'an Jiaotong University Press, May 31, 2017, May 31, 2017, 232.

\* cited by examiner

TOTAL FLAVONOIDS EXTRACT OF GYNURA FORMOSANA KITAM., PREPARATION METHOD THEREFOR AND USE THEREOF FOR TREATING HYPERURICEMIA

CROSS-REFERENCE TO RELATED APPLICATIONS

This application is a continuation application of International Patent Application No. PCT/CN2018/101168 with an international filing date of Aug. 17, 2018, designating the United States, now, and further claims priority benefits to Chinese Patent Application No. 201710841633.9, filed on Sep. 18, 2017. The contents of all of the aforementioned applications are incorporated herein by reference.

TECHNICAL FIELD

The present invention belongs to the field of medicines or health products, and particularly relates to a total flavonoid extract from Gynura formosana Kitam., and preparation method thereof, and use of same for treating hyperuricemia.

BACKGROUND OF THE INVENTION

Gout is a metabolic disease caused by the increased level of blood uric acid due to purine metabolic disorders and (or) the reduction of uric acid excretion, and the deposition of single sodium urate crystals on joints, cartilage, kidney, and the like. The main manifestation of gout includes recurrent redness, swelling, fever, pain and dysfunction of joints, even joint deformity, renal stone disease and urine acidic nephropathy. Hyperuricemia caused by reduction of uric acid excretion or generation of increased uric acid is the main cause of gout. Hyperuricemia is not only a direct cause of gout, but also is closely related to metabolic syndrome, type II diabetes, hypertension, cardiovascular disease, chronic kidney disease and the like. The pathogenesis of hyperuricemia and gout is related to genetic factors, environmental factors, glycogen accumulation diseases, renal insufficiency, hemopathy and medicines, etc.

In recent years, the prevalence of gout and hyperuricemia rises year by year. The epidemiological study shows that the prevalence of hyperuricemia in adult is 8.4% in China. The male has a higher prevalence of 9.9% than the female who has a prevalence of 7.0%. Urban residents have an obviously higher prevalence of 14.9% than rural residents who have a prevalence of 6.6%. Populations in regions with relatively high real GDP per capita also have higher prevalence of hyperuricemia.

Currently, the medicine for resisting hyperuricemia mainly comprises three categories: i.e. xanthine oxidase inhibitor, urate anion transporter 1 (URAT1) inhibitor and uricase. The medicine clinically used for regulating the metabolism of uric acid includes allopurinol, probenecid and the like, and the medicine for treating acute gouty arthritis includes colchicine, non-steroidal anti-inflammatory drug, glucocorticoid and the like. However, these medicines have a number of side effects, such as headache, rash, edema, gastrointestinal bleeding, chronic renal papillary necrosis and lethal hypersensitivity syndrome, and the like, which greatly limits their clinical applications.

Plant drugs have been traditionally used for treating hyperuricemia and gout in China, India, Canada, etc. since ancient times.

*Gynura formosana* Kitam. also called Bai Bei Tian Kui and Pien Tze Huang grass, is a herbaceous perennial plant of the genus Gynura Cass. nom. Cons. in the composite family. *Gynura formosana* Kitam. contains rich vitamins, alkaloids and flavonoid substances, and can be used for both medicine and food. Studies show that *Gynura formosana* Kitam. is mainly used for the treatment of diseases such as pneumonia, lung cancer, hepatitis, liver cirrhosis, hypertension and the like, and also has the effects of clearing away heat and toxic materials.

Currently, there are no related reports for the treatment of hyperuricemia with extracts from *Gynura formosana* Kitam. in the prior art.

SUMMARY OF THE INVENTION

The objective of the present invention is to provide a total flavonoid extract from *Gynura formosana* Kitam., and further provide a preparation method thereof and use of same.

The objective of the present invention is realized by the following technical solutions:

In a first aspect, the present invention provides a total flavonoid extract from *Gynura formosana* Kitam., comprising, in weight percent, 80-85% of rutin.

In a second aspect, the present invention also provides a preparation method of the total flavonoid extract from *Gynura formosana* Kitam., comprising the steps of:

(1) Extraction: extracting *Gynura formosana* Kitam., with an extraction solvent to obtain an extraction solution, and adjusting the extraction solution to a pH of 4-8 to obtain a reaction solution;

(2) Enzymolysis: adding a complex enzyme into the reaction solution to carry out enzymolysis through a forced circular reaction at a temperature of 30° C. to 50° C. for 1 to 4 hours, then carrying out suction filtration, and collecting a filtrate;

(3) Extraction and concentration: extracting the filtrate by using a macroporous resin A to obtain an extracted solution, and concentrating the extracted solution to obtain a concentrated solution;

(4) Separation and purification: centrifuging the concentrated solution, collecting a supernatant and carrying out elution by using a macroporous resin B, measuring absorbance at a wavelength of 510 nm, collecting eluate, concentrating and drying the eluate to obtain an extract.

Preferably, in the above preparation method, the complex enzyme used in the enzymolysis step consists of papain, cellulase and pectinase.

Preferably, in the above preparation method, a weight ratio of the complex enzyme to the *Gynura formosana* Kitam. is 1:5 to 1:3.

Preferably, in the above preparation method, a weight ratio of papain to cellulase to pectinase in the complex enzyme is (0.5-1.5):(2-5):(1-3).

Preferably, in the above preparation method, the weight ratio of papain to cellulase to pectinase in the complex enzyme is 1:3:2.

Preferably, in the above preparation method, the macroporous resin A is one or more selected from the group consisting of AB-8, DM-130, HZ841, ZH-00, ZH-01, ZH-02, ZH-03, CAD-40, CAD-45 and BS-30; and the macroporous resin B is one or more selected from the group consisting of D-101, D-140, D-141, XAD-3, XAD-4, HP-20, HP-21, LD-605 and LSA-10.

Preferably, in the above preparation method, the extraction solvent in the extraction step is water, and a weight ratio of *Gynura formosana* Kitam. to water is 1:(20-60).

Preferably, in the above preparation method, in the separation and purification step, an ethanol aqueous solution with a volume concentration of 70-80% is adopted as an elution solvent, and the elution is performed at a rate of 3-15 m/h.

Preferably, in the above preparation method, in the separation and purification step, an ethanol aqueous solution with a volume concentration of 75% is adopted as an elution solvent, and the elution is performed at a rate of 5 m/h.

Preferably, in the above preparation method, the concentrated solution comprises total flavonoid from *Gynura formosana Kitam.* at a concentration of 0.5 mg/mL.

Preferably, in the above preparation method, the extraction and concentration step comprises: placing the filtrate into an extraction tank containing a macroporous resin A, stirring at 30° C. for 6 to 24 hours at 80-150 rpm, then filtering to obtain an absorbed macroporous resin A, adding ethanol solution having a volume concentration of 70-95% to the absorbed macroporous resin A, wherein the ethanol solution is added in an amount 10 to 30 times the weight of the absorbed macroporous resin A, followed by stirring at 30° C. for 6 to 24 hours at 80-150 rpm, and filtering to obtain an extracted solution.

Preferably, in the above preparation method, said adjusting the extraction solution to a pH of 4-8 is carried out with a hydrochloric acid or sodium hydroxide.

Preferably, in the above preparation method, said drying refers to freeze drying.

In a further aspect, the present invention provides a total flavonoid extract from *Gynura formosana Kitam.* prepared by the above preparation method.

In a further aspect, the present invention provides a pharmaceutical preparation, comprising the above mentioned total flavonoid extract from *Gynura formosana Kitam.* or a total flavonoid extract from *Gynura formosana Kitam.* prepared by the above preparation method as an active ingredient, wherein the active ingredient is mixed with a conventional auxiliary material and prepared according to a conventional process into clinically acceptable forms selected from the group consisting of tablets, capsules, powders, mixtures, pills, granules, syrups, plasters, suppositories, aerosols, ointments and injections.

The conventional auxiliary material can be selected from the group consisting of fillers, disintegrants, lubricants, suspending agents, adhesives, sweeteners, flavoring agents, preservatives, matrix and the like. Fillers include starch, pre-gelatinized starch, lactose, mannitol, chitin, microcrystalline cellulose, sucrose, and the like. Disintegrants include starch, pre-gelatinized starch, microcrystalline cellulose, sodium carboxymethyl starch, cross-linked polyvinylpyrrolidone, low substituted hydroxypropyl cellulose, croscarmellose sodium, and the like. Lubricants include magnesium stearate, sodium dodecyl sulfate, talcum powder, silicon dioxide and the like. Suspending agents include polyvinylpyrrolidone, microcrystalline cellulose, sucrose, agar, hydroxypropyl methyl cellulose and the like. Adhesives include starch slurry, polyvinylpyrrolidone, hydroxypropyl methyl cellulose and the like. Sweeteners include sodium saccharin, aspartame, sucrose, sodium cyclamate, glycyrrhetinic acid and the like. Flavoring agents include a sweetener and various essences. Preservatives include paraben, benzoic acid, sodium benzoate, sorbic acid and salts thereof, benzalkonium bromide, chloroethyl acetate, *eucalyptus* oil and the like. The matrix comprises PEG 6000, PEG 4000, insect wax and the like.

In a further aspect, the present invention provides use of the above total mentioned flavonoid extract from *Gynura formosana Kitam.* or a total flavonoid extract from *Gynura formosana Kitam.* prepared by the above preparation method or the above mentioned pharmaceutical preparation in preparing drug or health product for treating hyperuricemia.

In a further aspect, the present invention provides use of the above total mentioned flavonoid extract from *Gynura formosana Kitam.* or a total flavonoid extract from *Gynura formosana Kitam.* prepared by the above preparation method or the above mentioned pharmaceutical preparation in preparing drug or health product for treating gout.

The technical solutions of the present invention have the following advantages:

(1) According to the invention, a total flavonoid extract containing 80-85% rutin is extracted and separated. The efficacy experiment results show that the extract can reduce activity of xanthine oxidase in liver of hyperuricemia model mice to a certain extent, reduce uric acid synthesis, have certain uric acid reduction effect, and can be used as a potential medicine for treating hyperuricemia or treating gout.

(2) In the present preparation method of the total flavonoid extract from *Gynura formosana Kitam.*, a unique complex enzyme which comprises specific enzymes at specific ratio is adopted for carrying out enzymolysis at 30° C. to 50° C. after the extraction step, so that the structure of the total flavonoid extract is prevented from being damaged at high temperatures, and the total flavonoid compounds can be extracted out to the maximum extent. Further, extraction and concentration with a macroporous resin A and separation and purification with a macroporous resin B are carried out, so that the extraction rate of the total flavonoid compounds of the *Gynura formosana Kitam.* can reach 1.8-2.0%, which is 30% or more higher compared with the extraction rate of the total flavonoid compounds by the existing method. The HPLC purity of rutin in the prepared total flavonoid extract can reach 80-85%.

BRIEF DESCRIPTION OF THE DRAWINGS

The present invention is described in detail with reference to examples and accompanying drawings, wherein.

DETAILED DESCRIPTION OF THE EMBODIMENTS

*Gynura formosana Kitam.* used in the following examples and experimental example of the present invention are taken from Dengke village, Longwen disctrict, Zhangzhou city, Fujian Province, and are identified as the *Gynura formosana Kitam.*

Example 1

Figure 1:
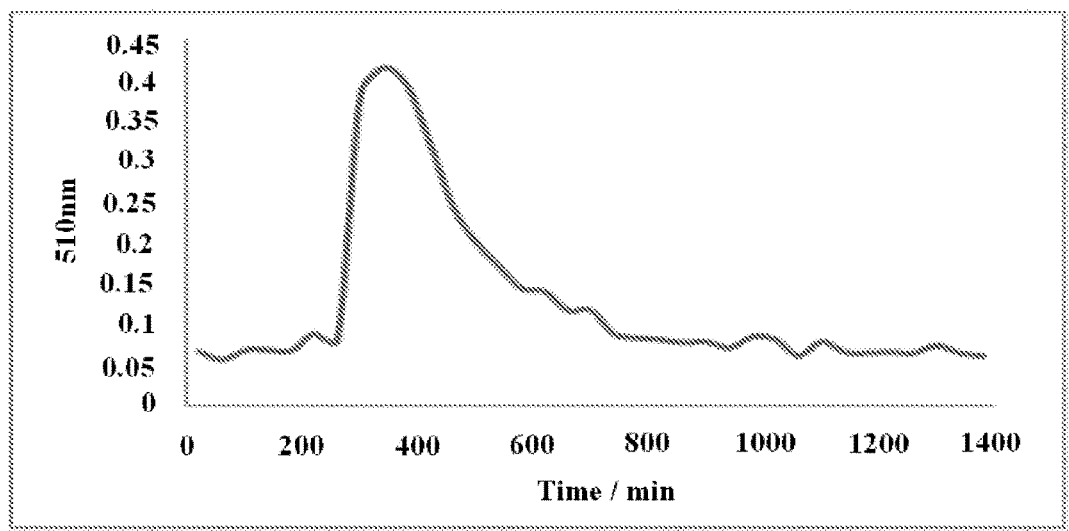
FIG. 1 shows an elution curve in Example 1 of the present invention.

A total flavonoid extract from *Gynura formosana Kitam.* is prepared according to the following method:

(1) Extraction: 100 g *Gynura formosana Kitam.* was added into water with a weight 30 times the weight of *Gynura formosana Kitam.* to carry out extraction, producing an extraction solution, which was then adjusted with a diluted hydrochloric acid to a pH of 5, obtaining a reaction solution;

(2) Enzymolysis: 25 g of complex enzyme consisting of papain, cellulase and pectinase with a weight ratio of 1:3:2 was added into the reaction solution to carry out enzymolysis through a forced circular reaction at 40° C. for 3 hours, and the resulted solution was suction filtered and a filtrate was collected;

(3) Extraction and Concentration: The filtrate was added to an extraction tank containing AB-8 macroporous resin and stirred for 12 hours at 30° C. and 100 rpm, then filtered to obtain an absorbed AB-8 macroporous resin. An ethanol solution with a volume concentration of 75% was added to the absorbed AB-8 macroporous resin at an amount 20 times the weight of the absorbed AB-8 macroporous resin, then stirred for 12 hours at 30° C. and 120 rpm and then filtered to obtain an extracted solutions. The extracted solution was vacuum concentrated to produce a concentrated solution which comprises a total flavonoid extract from *Gynura formosana Kitam.* at a concentration of 0.5 mg/mL;

(4) Separation and Purification: The concentrated solution was centrifuged at 10,000 rpm for 10 minutes, and a supernatant was collected and placed into a chromatographic column filled with a macroporous resin D-101 for stationary adsorption for 60 min. Then the column was eluted with an aqueous solution of ethanol with a volume concentration of 75% at a rate of 5 m/h, and absorbance was measured at a wavelength of 510 nm. An elution curve was plotted with absorbance as Y-axis versus elution time as X-axis, as shown in FIG. 1. Eluate corresponding to the absorption peak area of the elution curve was collected, concentrated, and freeze-dried to obtain the total flavonoid extract from *Gynura formosana Kitam.*

Through calculation, the extraction rate of the total flavonoid extract from *Gynura formosana Kitam.* is 2.0%.

By referring to FIG. 1, the elution curve of the eluate shows a significant single absorption peak at 340 min, indicating the relatively pure flavonoid in the eluate.

A. The total flavonoid extract from *Gynura formosana Kitam.* was identified with an infrared spectrum according to the following method:

The method comprises the following steps: A certain amount of dried rutin standard was mixed with dried potassium bromide at a weight ratio of 1:100, ground and prepared into a solid pellet. The pellet was then tested with a Fourier infrared spectrophotometer within a scanning range of 4000 cm$^{-1}$ to 400 cm$^{-1}$, a resolution of 4 and a scanning number of 4, thereby obtaining an infrared spectrum. The total flavonoid extract from *Gynura formosana Kitam.* was tested in the same manner to obtain an infrared spectrum. The results are shown in FIG. 2.

Figure 2:
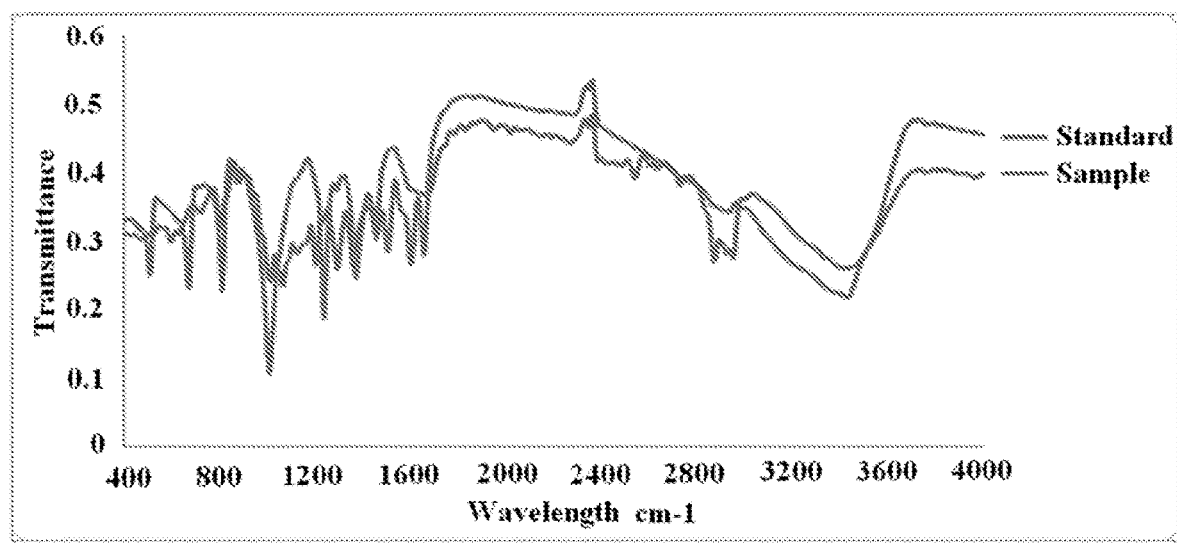
FIG. 2 shows an infrared spectrum of a total flavonoid extract from *Gynura formosana Kitam.* prepared in Example 1 of the present invention.

By referring to FIG. 2, both the infrared spectrums of the rutin standard and the total flavonoid extract from *Gynura formosana Kitam.* show a wide and strong absorption peak around 3685.455 cm$^{-1}$ to 3018.177 cm$^{-1}$, corresponding to telescopic vibration peak of —OH, indicating there are large amount of phenolic hydroxyl groups or sugar hydroxyl groups. A weak absorption peak occurs at 2914.036 cm$^{-1}$, corresponding to a telescopic vibration peak of a carbon-hydrogen bond, indicating less hydrogen on saturated carbon. A strong peak appears at 1654.694 cm$^{-1}$ in each spectrum, corresponding to a telescopic vibration of C=O. The peaks in the two spectrums appear at substantially same position and have substantially same shape, indicating that the extract is a flavonoid. Bending vibration peak of hydroxyl groups appears at 1371.88 cm$^{-1}$ and 1362.89 cm$^{-1}$. An absorption peak caused by ortho hydrogens of phenyl ring appears at 804.80 cm$^{-1}$ and 810.56 cm$^{-1}$. An absorption peak caused by the position of a substituent on the phenyl ring appears at 1010.07 cm$^{-1}$ to 696.62 cm$^{-1}$, but the peak position is different in the two spectrum, indicating the hydroxyl substitution position of the extract is different from that of the rutin standard. These results indicate that the extract contains hydroxyl, carbonyl, and other functional groups such as different position-substituted benzene rings, and the characteristic absorption peaks are substantially consistent. Thus, it can be determined that the extract is a flavonoid compound.

B. The total flavonoid extract from *Gynura formosana Kitam.* was analyzed by liquid chromatography to determine the content of rutin therein according to the following method:

B1. Liquid Chromatography Conditions

Liquid Chromatography Conditions are as follows:

Eclipse XDB-C18 AnalyticalGuard Column (4.6×12.5 mm, 5 μm) and ZOR BZX Eclipse XDB-C18 Column (4.6×150 mm, 5 μm) were used as a protection column. Flow rate is 0.5 mL/min; Column temperature is 35° C. Detection wavelength is 368 nm, 254 nm and 210 nm, respectively; Sample loading volume is 10 μL; Mobile phases consists of (A) 0.03% formic acid aqueous solution and (B) Acetonitrile; Gradient elution procedures are as follows: 0-10 min, 80% (A) and 20% (B); 10-12 min, 76% to 80% (A) and 20% to 24% (B); 12-20 min, 76% (A) and 24% (B); 20-25 min, 70% to 76% (A) and 24% to 30% (B); 25-48 min, 70% (A) and 30% (B).

B2. Preparation of Control Sample Solution 0.001 g Rutin was weighed accurately and dissolved in 1 mL of methanol to prepare a single control sample solution of 1 mg/mL. The control sample solution was filtered with a disposable filter and then loaded into a small test tube for later use.

B3. Determination

The control sample solution and a test sample solution (1 μg/μL methanol solution of the total flavonoid extract prepared in Example 1) are respectively accurately sucked and injected to the liquid chromatography column to perform analysis according to the above mentioned liquid chromatography conditions.

Figure 3:
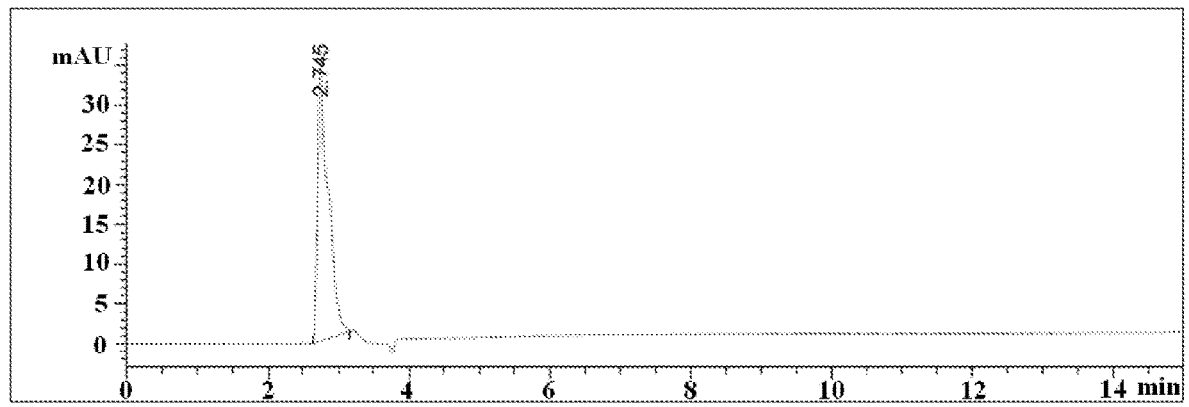
FIG. 3 shows a HPLC chromatogram of a rutin control solution in Example 1 of the present invention.
Figure 4:
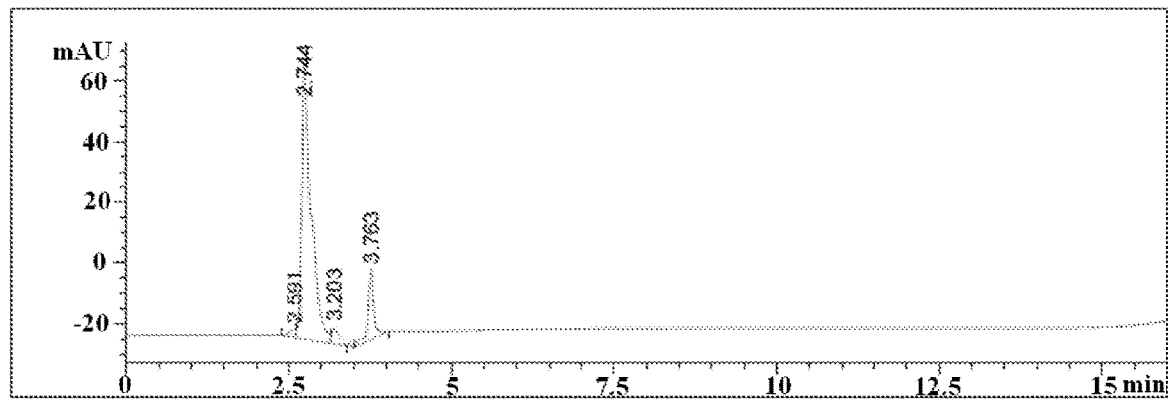
FIG. 4 shows a HPLC chromatogram of the total flavonoid extract from *Gynura formosana Kitam.* prepared in Example 1 of the present invention.

The HPLC chromatogram of the control sample solution is shown in FIG. 3, and the HPLC chromatogram of the test sample solution is shown in FIG. 4.

By referring to FIG. 3, the rutin control solution can be completely isolated within 10 minutes. A substantially straight baseline is observed in the chromatogram of Rutin under the chromatographic conditions of this experiment, and peak tailing is not observed. There are no interfering peaks of impurities. The peaks appear earlier and the retention time is 2.745 min.

By referring to FIG. 4, the amount of rutin in the extract was 81.29% as calculated by area normalization.

Example 2

A total flavonoid extract from *Gynura formosana Kitam.* is prepared according to the following method:
(1) Extraction: 100 g *Gynura formosana Kitam.* was added into water with a weight 20 times the weight of *Gynura formosana Kitam.* to carry out extraction, producing an extraction solution, which was then adjusted with diluted sodium hydroxide solution to a pH of 8, obtaining a reaction solution;
(2) Enzymolysis: 20 g of complex enzyme consisting of papain, cellulase and pectinase with a weight ratio of 0.5:5:1 was added into the reaction solution to carry out enzymolysis through a forced circular reaction at 30° C. for 4 hours, and the resulted solution was suction filtered and a filtrate was collected;
(3) Extraction and Concentration: The filtrate was added to an extraction tank containing DM-130 macroporous resin and stirred for 24 hours at 30° C. and 80 rpm, then filtered to obtain an absorbed DM-130 macroporous resin. An ethanol solution with a volume concentration of 95% was added to the absorbed DM-130 macroporous resin at an amount 10 times the weight of the absorbed DM-130 macroporous resin, then stirred for 24 hours at 30° C. and 80 rpm and then filtered to obtain an extracted solution. The extracted solution was vacuum concentrated to produce a concentrated solution which comprises a total flavonoid extract from *Gynura formosana Kitam.* at a concentration of 0.5 mg/mL;
(4) Separation and Purification: The concentrated solution was centrifuged at 6,000 rpm for 8 minutes, and a supernatant was collected and placed into a chromatographic column filled with a macroporous resin HP-21 for stationary adsorption for 60 min. Then the column was eluted with an aqueous solution of ethanol with a volume concentration of 80% at a rate of 3 m/h, and absorbance was measured at a wavelength of 510 nm. An elution curve was plotted with absorbance as Y-axis versus elution time as X-axis. Eluate corresponding to the absorption peak area of the elution curve was collected, concentrated, and freeze-dried to obtain the total flavonoid extract from *Gynura formosana Kitam.*

Through calculation, the extraction rate of the total flavonoid extract from *Gynura formosana Kitam.* is 1.82%.

The total flavonoid extract from *Gynura formosana Kitam.* was analyzed by liquid chromatography to determine the content of rutin therein according to the method as described in section B of example 1. According to the resulted HPLC chromatogram, the amount of rutin in the total flavonoid extract was 80% in this example.

Example 3

A total flavonoid extract from *Gynura formosana Kitam.* is prepared according to the following method:
(1) Extraction: 100 g *Gynura formosana Kitam.* was added into water with a weight 60 times the weight of *Gynura formosana Kitam.* to carry out extraction, producing an extraction solution, which was then adjusted with a diluted hydrochloric acid to a pH of 4, obtaining a reaction solution;
(2) Enzymolysis: 32 g of complex enzyme consisting of papain, cellulase and pectinase with a weight ratio of 1.5:2:3 was added into the reaction solution to carry out enzymolysis through a forced circular reaction at 50° C. for 1 hour, and the resulted solution was suction filtered and a filtrate was collected;
(3) Extraction and Concentration: The filtrate was added to an extraction tank containing ZH-01 macroporous resin and stirred for 6 hours at 30° C. and 150 rpm, then filtered to obtain an absorbed ZH-01 macroporous resin. An ethanol solution with a volume concentration of 70% was added to the absorbed ZH-01 macroporous resin at an amount 30 times the weight of the absorbed ZH-01 macroporous resin, then stirred for 6 hours at 30° C. and 150 rpm and then filtered to obtain an extracted solution. The extracted solution was vacuum concentrated to produce a concentrated solution which comprises a total flavonoid extract from *Gynura formosana Kitam.* at a concentration of 0.5 mg/mL;
(4) Separation and Purification: The concentrated solution was centrifuged at 8,000 rpm for 5 minutes, and a supernatant was collected and placed into a chromatographic column filled with a macroporous resin XAD-3 for stationary adsorption for 60 min. Then the column was eluted with an aqueous solution of ethanol with a volume concentration of 70% at a rate of 15 m/h, and absorbance was measured at a wavelength of 510 nm. An elution curve was plotted with absorbance as Y-axis versus elution time as X-axis. Eluate corresponding to the absorption peak area of the elution curve was collected, concentrated, and freeze-dried to obtain the total flavonoid extract from *Gynura formosana Kitam.*

Through calculation, the extraction rate of the total flavonoid extract from *Gynura formosana Kitam.* is 1.91%.

The total flavonoid extract from *Gynura formosana Kitam.* was analyzed by liquid chromatography to determine the content of rutin therein according to the method as described in section B of example 1. According to the resulted HPLC chromatogram, the amount of rutin in the total flavonoid extract was 85% in this example.

Experiment Example 1

Experiment study on anti-gout effects of the total flavonoid extract from *Gynura formosana Kitam.*
1. Experimental Objectives The mouse model of hyperuricemia was established by intraperitoneal injection of xanthine to increase the content of uric acid precursor in the body and thus to increase the generation of uric acid. The mouse model of hyperuricemia was administered via gavage with the total flavonoid extract from *Gynura formosana Kitam.* The inhibition rates of uric acid and anhydride in serum of the mouse and the inhibition rate of the activity of xanthine oxidase in the liver of the mouse were recorded to study the effect of the total flavonoid extract on symptoms of gout caused by hyperuricemia.
2. Experimental Materials
2.1 Experimental Animals 84 male mice of clean grade, each weighing 28±2 g, were purchased from WU Animal Center. All of the mice were kept in an air-conditioned room at a room temperature of 22±2° C. and a humidity of (60±5) %, fed with standard granular feed, and given free access to water and feed.
2.2 Drugs The following drugs were used: Total flavonoid extract from *Gynura formosana Kitam.*; allopurinol tablets (Hefei Jiulian Pharmaceutical Co., Ltd., Lot No: 20140401); Gouty tablets (Changchun overseas pharmaceutical, Lot No.: 1309105); Xanthine (Aladdin); Saline; Uric acid kit (Nanjing Jiancheng Bioengineering Institute, Product code: C012, Production Lot No.: 20140918), Xanthine Oxidase Kit (Nanjing Jiancheng Bioengineering Institute, Product code: A002, Production Lot No: 20140210); Creatinine (Cr) Test Kit (Nanjing Jiancheng Bioengineering Institute, Product code: C011-1).

2.3 Experimental Instruments

The following instruments were used: a low-speed centrifuge; a micropipette; a disposable syringe; a capillary vessel; a watch glass; a disposable centrifuge tube; surgical scissors; and a homogenizer.

3. Experimental Methods 3.1. Test Drug

A total flavonoid extract from *Gynura formosana Kitam.* was prepared according to the method as described in the example 1, and used as a test drug.

3.2 Gout Experiments 3.2.1 Anti-Gout Experiments on Mice 84 male Kunming mice, each weighing 28±2 g, were randomly divided into 7 groups: a control group, a model group, a group of gouty tablets, a group of allopurinol, a high dose group of the total flavonoid extract, a medium dose group of the total flavonoid extract and a low dose group of the total flavonoid extract. The group of gouty tablets and the group of allopurinol, used as positive groups, were administered with gouty tablets at a dose of 9.6 mg/10 g and allopurinol at a dose of 0.2 m/10 g, respectively. The high, medium and low dose groups of the total flavonoid extract were administered via gavage with an aqueous solution of total flavonoid extract from *Gynura formosana Kitam.* at a dose of 24 mg/10 mL, 12 mg/10 mL, 6 mg/10 mL, respectively. The model group was administered an equal-volume of saline. All of the drugs were administered once daily for continuous 11 days.

3. 2.2 Uric Acid and Creatinine Indexes in Serum of the Mice

After 1 hour at last administration, the mice received 10% xanthine dissolved in 0.8% CMC-Na via intraperitoneal injection. After 0.5 hours of modeling, the mice were sacrificed and blood was taken from eyeballs. Then the mice were dissected immediately and livers were taken and stored at a low temperature. The blood samples were centrifuged at 3000 r/min for 5 min, and serum was collected. Determinations of uric acid and creatinine were carried out according to the instructions of kits.

3. 2.3 Determination of Activity of Xanthine Oxidase (XOD) in Liver

The mice were sacrificed immediately after the blood was taken, and livers were rapidly taken out, weighed, placed into 10% homogenate prepared with saline pre-cooled to 4° C., and centrifuged for 10 min at 3000 r/min to produce a supernatant. Determination of the activity of xanthine oxidase was carried out according to the instructions of the kit.

3.4 Statistical Analysis of Data

The index was calculated by referring to the instructions. Data of each group were presented in the form of mean value±standard deviation (xva). Statistical analysis was carried out using SPSS 20.0 software, and the difference among groups was verified by a single-factor variance.

4. Experimental Results 4.1 Determinations of Uric Acid and Creatinine Levels in Serum of the Mice The effect of the total flavonoid extract on the uric acid level in serum of the mice is shown in Table 1.

TABLE 1

Effect of the total flavonoid extract from *Gynura formosana* Kitam. on uric acid levels in serum of the mice (xce)

| Group | Number of mice (n) | Dose g/10 g | Uric Acid (mg/L) | Creatinine (μmol/L) |
|---|---|---|---|---|
| Control group | 12 | — | 20.57 ± 4.92 | 0.023 ± 0.004 |
| Model group | 12 | — | 40.46 ± 3.36## | 0.022 ± 0.002 |
| Group of gouty tablets | 12 | 0.0096 | 27.53 ± 1.53 * | 0.023 ± 0.003 |
| Group of allopurinol | 12 | 0.0002 | 22.71 ± 0.27 ** | 0.023 ± 0.001 |
| High dose group of the total flavonoid extract | 12 | 0.12 | 23.03 ± 3.47 ** | 0.020 ± 0.002 |
| Medium dose group of the total flavonoid extract | 12 | 0.06 | 32.86 ± 1.13 * | 0.017 ± 0.000 |
| Low dose group of the total flavonoid extract | 12 | 0.03 | 31.38 ± 1.75 * | 0.019 ± 0.001 |

Note:
Compared with the control group, #$P < 0.01$, ##$P < 0.001$;
Compared with the model group, * $P < 0.01$, ** $P < 0.001$.

Table 1 shows that:

(1) After the drugs for modeling were administered, the uric acid level in serum of the model group was obviously increased, and the difference compared with the control group was statistically significant ($P<0.001$), indicating that the model was successfully established;

(2) After the drugs for treatment were administered, mice in the high, medium and low dose groups of the total flavonoid extract exhibited a certain decrease in the uric acid level, and the difference compared with the model group was obviously statistically significant ($P<0.01$). The content of creatinine in serum of each group did not show obvious difference.

4. 2 Determination of Xanthine Oxidase Level in Liver of the Mice

The effect of the total flavonoid extract on xanthine oxidase level in liver (XOD) of the mice is shown in Table 2.

TABLE 2

Effect of the total flavonoid extract from *Gynura formosana* Kitam. on xanthine oxidase level in liver of the mice ($\bar{x} \pm s$)

| Group | Number of mice (n) | XOD (U/gprot) |
|---|---|---|
| Control group | 12 | 29.54 ± 1.73 |
| Model group | 12 | 44.62 ± 1.96## |
| Group of gouty tablets | 12 | 40.64 ± 1.33 |
| Group of allopurinol | 12 | 35.44 ± 1.69** |
| High dose group of the total flavonoid extract | 12 | 37.06 ± 1.19* |

TABLE 2-continued

Effect of the total flavonoid extract from Gynura formosana Kitam. on xanthine oxidase level in liver of the mice ($\bar{x} \pm s$)

| Group | Number of mice (n) | XOD (U/gprot) |
|---|---|---|
| Medium dose group of the total flavonoid extract | 12 | 34.89 ± 3.01** |
| Low dose group of the total flavonoid extract | 12 | 45.27 ± 2.24 |

Note:
Compared with the control group, ##P < 0.01;
Compared with the model group, *P < 0.05, **P < 0.01.

Table 2 shows that:
(1) The difference between the control group and the model group was significant (P<0.01), indicating the model was successfully established;
(2) Mice in the medium dose group and the high dose group exhibited obviously decreased activity of xanthine oxidase in liver compared with the model group, and the difference is statistically significant (P<0.01, P<0.05), but mice in the low dose group did not show statistically significant difference compared with the model group. The results indicate that the total flavonoid extract from *Gynura formosana* Kitam. at high dose and medium dose can reduce the activity of xanthine oxidase in liver of the mice of the hyperuricemia model and can reduce the synthesis of uric acid to a certain extent, so it has a certain effect of reducing uric acid.

It is to be understood that the above-described examples are merely illustrative of the embodiments and are not intended to limit the embodiments. It will be apparent to one of ordinary skill in the art that other different forms of changes or variations can be made on the basis of the above description. It is to be understood that various changes or modifications may be made herein without departing from the scope of the invention as defined by the appended claims.

The invention claimed is:

1. A method for treating hyperuricemia or gout, comprising the step of administrating a total flavonoid extract from *Gynura formosana* Kitam. to a subject in need, wherein the total flavonoid extract from *Gynura formosana* Kitam., comprises, in weight percent, 80-85% of rutin and wherein the total flavonoid extract from *Gynura formosana* Kitam. is prepared by the steps of:
  (1) Extraction: extracting *Gynura formosana* Kitam. with an extraction solvent to obtain an extraction solution, and adjusting the extraction solution to a pH of 4-8 to obtain a reaction solution;
  (2) Enzymolysis: adding a complex enzyme into the reaction solution to carry out enzymolysis through a forced circular reaction at a temperature of 30° C. to 50° C. for 1 to 4 hours, then carrying out suction filtration, and collecting a filtrate;
  (3) Extraction and Concentration: extracting the filtrate by using a macroporous resin A to obtain an extracted solution, and concentrating the extracted solution to obtain a concentrated solution; and
  (4) Separation and Purification: centrifuging the concentrated solution, collecting a supernatant and carrying out elution by using a macroporous resin B, measuring absorbance at a wavelength of 510 nm, collecting eluate, concentrating and drying the eluate to obtain an extract.

2. The method of claim 1, wherein the complex enzyme used in the enzymolysis step consists of papain, cellulase and pectinase; and wherein a weight ratio of the complex enzyme to the *Gynura formosana* Kitam. is 1:5 to 1:3.

3. The method of claim 1, wherein a weight ratio of papain to cellulase to pectinase in the complex enzyme is (0.5-1.5):(2-5):(1-3).

4. The method of claim 1, wherein the macroporous resin A is one or more selected from the group consisting of AB-8, DM-130, HZ841, ZH-00, ZH-01, ZH-02, ZH-03, CAD-40, CAD-45 and BS-30; and the macroporous resin B is one or more selected from the group consisting of D-101, D-140, D-141, XAD-3, XAD-4, HP-20, HP-21, LD-605 and LSA-10.

5. The method of claim 1, wherein in the extraction step, the extraction solvent is water, and a weight ratio of *Gynura formosana* Kitam. to water is 1:(20-60).

6. The method of claim 1, wherein:
  in the separation and purification step, an ethanol aqueous solution with a volume concentration of 70-80% is adopted as an elution solvent, and the elution is performed at a rate of 3-15 m/h; and
  the concentrated solution comprises total flavonoid from *Gynura formosana* Kitam. at a concentration of 0.5 mg/mL.

7. The method of claim 2, wherein a weight ratio of papain to cellulase to pectinase in the complex enzyme is (0.5-1.5):(2-5):(1-3).

8. The method of claim 7, wherein the weight ratio of papain to cellulase to pectinase in the complex enzyme is 1:3:2.

9. The method of claim 2, wherein the macroporous resin A is one or more selected from the group consisting of AB-8, DM-130, HZ841, ZH-00, ZH-01, ZH-02, ZH-03, CAD-40, CAD-45 and BS-30; and the macroporous resin B is one or more selected from the group consisting of D-101, D-140, D-141, XAD-3, XAD-4, HP-20, HP-21, LD-605 and LSA-10.

10. The method of claim 2, wherein in the extraction step, the extraction solvent is water, and a weight ratio of *Gynura formosana* Kitam. to water is 1:(20-60).

11. The method of claim 2, wherein:
  in the separation and purification step, an ethanol aqueous solution with a volume concentration of 70-80% is adopted as an elution solvent, and the elution is performed at a rate of 3-15 m/h; and
  the concentrated solution comprises total flavonoid from *Gynura formosana* Kitam. at a concentration of 0.5 mg/mL.

12. The method of claim 3, wherein the weight ratio of papain to cellulase to pectinase in the complex enzyme is 1:3:2.

13. The method of claim 3, wherein the macroporous resin A is one or more selected from the group consisting of AB-8, DM-130, HZ841, ZH-00, ZH-01, ZH-02, ZH-03, CAD-40, CAD-45 and BS-30; and the macroporous resin B is one or more selected from the group consisting of D-101, D-140, D-141, XAD-3, XAD-4, HP-20, HP-21, LD-605 and LSA-10.

14. The method of claim 3, wherein in the extraction step, the extraction solvent is water, and a weight ratio of *Gynura formosana* Kitam. to water is 1:(20-60).

15. The method of claim 3, wherein:
  in the separation and purification step, an ethanol aqueous solution with a volume concentration of 70-80% is adopted as an elution solvent, and the elution is performed at a rate of 3-15 m/h; and
  the concentrated solution comprises total flavonoid from *Gynura formosana* Kitam. at a concentration of 0.5 mg/mL.

16. A method for treating hyperuricemia or gout, comprising the step of administering to a subject in need a pharmaceutical preparation comprising a total flavonoid extract from *Gynura formosana* Kitam. as an active ingredient, wherein the total flavonoid extract from *Gynura formosana* Kitam., comprises, in weight percent, 80-85% of rutin, wherein the active ingredient is mixed with a conventional auxiliary material and prepared according to a conventional process into clinically acceptable forms selected from the group consisting of tablets, capsules, powders, mixtures, pills, granules, syrups, plasters, suppositories, aerosols, ointments and injections; and wherein the total flavonoid extract from *Gynura formosana* Kitam. is prepared by the steps of:

(1) Extraction: extracting *Gynura formosana* Kitam. with an extraction solvent to obtain an extraction solution, and adjusting the extraction solution to a pH of 4-8 to obtain a reaction solution:

(2) Enzymolysis: adding a complex enzyme into the reaction solution to carry out enzymolysis through a forced circular reaction at a temperature of 30° C. to 50° C. for 1 to 4 hours, then carrying out suction filtration, and collecting a filtrate;

(3) Extraction and Concentration: extracting the filtrate by using a macroporous resin A to obtain an extracted solution, and concentrating the extracted solution to obtain a concentrated solution; and (4) Separation and Purification: centrifuging the concentrated solution, collecting a supernatant and carrying out elution by using a macroporous resin B, measuring absorbance at a wavelength of 510 nm, collecting eluate, concentrating and drying the eluate to obtain an extract.

\* \* \* \* \*